(12) United States Patent
Winkler et al.

(10) Patent No.: US 10,350,516 B2
(45) Date of Patent: Jul. 16, 2019

(54) BLOOD FILTERING DEVICE

(71) Applicant: Mann+Hummel GMBH, Ludwigsburg (DE)

(72) Inventors: Dagmar Winkler, Filderstadt (DE); Heike Rupp, Stuttgart (DE); Steffen Schuetz, Bietigheim-Bissingen (DE); Karlheinz Muenkel, Oberderdingen-Flehingen (DE); Joachim Stinzendoerfer, Speyer (DE)

(73) Assignee: MANN+HUMMEL GmbH, Ludwigsburg (DE)

( * ) Notice: Subject to any disclaimer, the term of this patent is extended or adjusted under 35 U.S.C. 154(b) by 771 days.

(21) Appl. No.: 14/981,396

(22) Filed: Dec. 28, 2015

(65) Prior Publication Data
US 2016/0129374 A1    May 12, 2016

Related U.S. Application Data

(63) Continuation of application No. PCT/EP2014/069355, filed on Sep. 11, 2014.

(30) Foreign Application Priority Data

Oct. 15, 2013    (DE) .................. 10 2013 017 036

(51) Int. Cl.
*A61M 1/02* (2006.01)
*B01D 27/06* (2006.01)
(Continued)

(52) U.S. Cl.
CPC .............. *B01D 27/06* (2013.01); *A61M 1/02* (2013.01); *B01D 27/08* (2013.01); *B01D 27/108* (2013.01); *G01N 33/491* (2013.01)

(58) Field of Classification Search
CPC ...... B01D 27/06; B01D 27/08; B01D 27/108; G01N 33/491; A61M 1/02
See application file for complete search history.

(56) References Cited

U.S. PATENT DOCUMENTS 5,626,759 A    5/1997    Krantz et al.
5,919,356 A    7/1999    Hood
(Continued)

FOREIGN PATENT DOCUMENTS

DE    102010030238 A1    12/2011

*Primary Examiner* — Vishal V Vasisth
(74) *Attorney, Agent, or Firm* — James Hasselbeck

(57) ABSTRACT

A blood filtering device has a tubular housing with a tubular section and tubular housing volume. A filtration section with a filter medium separating a raw side from a clean side is arranged in the tubular housing. The filtration section is movable along the tubular section and movably sealed relative to the tubular housing. The filtration section separates the tubular housing volume into variable first and second tubular housing volumes. A first communication path extends between raw side and first tubular housing volume. A second communication path exits between raw side and second tubular housing volume. When moving the filtration section, blood in the first tubular housing volume flows through the first communication path to the raw side; blood plasma passes through the filter medium to the clean side; residual blood flows through the second communication path into the variable second tubular housing volume.

15 Claims, 3 Drawing Sheets

(51) Int. Cl.
  *B01D 27/08* (2006.01)
  *B01D 27/10* (2006.01)
  *G01N 33/49* (2006.01)

(56) References Cited

U.S. PATENT DOCUMENTS

| | | | |
|---|---|---|---|
| 5,935,437 A * | 8/1999 | Whitmore | A61M 1/3496 206/438 |
| 6,010,627 A | 1/2000 | Hood, III | |
| 2011/0100921 A1 | 5/2011 | Heinrich | |

* cited by examiner

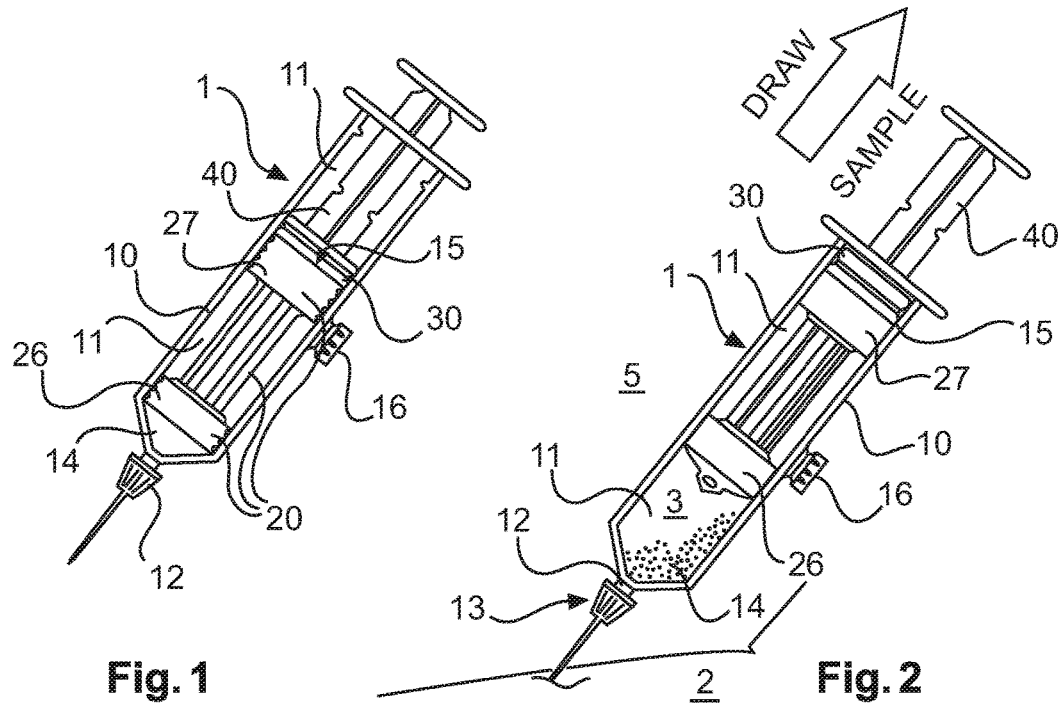
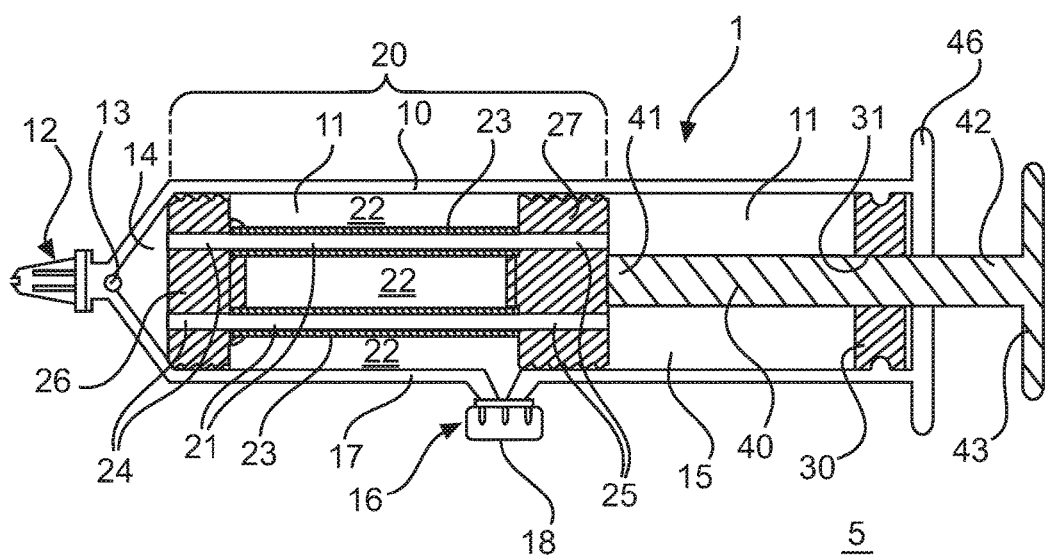

EXTRACT PLASMA

BLOOD FILTERING DEVICE

CROSS-REFERENCE TO RELATED APPLICATIONS

This application is a continuation application of international application No. PCT/EP2014/069355 having an international filing date of 11 Sep. 2014 and designating the United States, the international application claiming a priority date of 15 Oct. 2013, based on prior filed German patent application No. 10 2013 017 036.2, the entire contents of the aforesaid international application and the aforesaid German patent application being incorporated herein by reference

BACKGROUND OF THE INVENTION

The present invention relates to a device for blood filtering, in particular to a filtering device enabling a quick and simple filtration process for the separation of blood cells.

Blood filtering is required for the separation of the specific components of the human blood. In particular, separation is required as particular analysis may be carried out only on particular components of the human blood and other blood components may disturb the analysis. Human blood is comprised of different components, for example erythrocytes (red blood cells) which may have a size of about 7-8 µm; leucocytes (white blood cells) which may have a size of about 8 to 20 µm; thrombocytes (platelets) which may have a size of about 1.5 to 3 µm; and blood plasma. The erythrocytes, the leucocytes, and the thrombocytes represent more than 40 vol.-% of the whole blood. In order to separate the different components of the human blood, a centrifugation process has been established. However, a centrifugation process requires a considerable amount of time and a rather complex apparatus. For particular purposes, it may be required to obtain a separation of the blood components in a short time and with an apparatus of minimum complexity. Further, it may be required to provide an apparatus which is easy to handle, in particular for urgent or emergency medical applications.

A subsequent whole blood separation into plasma/serum can be advantageous for point-of-care testing devices, which are used to provide a quick blood analysis at/near the patient to get a quick blood analysis result outside of a clinical laboratory to make immediate decisions about patient care. Typically, point-of-care testing is performed by non-laboratory personnel. A quick foregoing plasma filtration process facilitates the quick blood analysis and enables new operating conditions for point-of-care devices, since most of them work with whole blood or with the aforementioned micro devices which lead to a very small yield of plasma/serum volume. The whole blood separation process can also be integrated within the point-of-care device.

SUMMARY OF THE INVENTION

The present invention provides a blood filtering device in accordance with the independent claim that enables a quick separation of blood components and an easy handling of the filtering device. Further embodiments can be taken from the dependent claims.

According to the invention, there is provided a blood filtering device including a tubular housing and a filtration section, wherein the tubular housing has a tubular section and defines a tubular housing volume, wherein the filtration section comprises a raw side and a clean side separated by a filter medium, wherein the filtration section is movable along the tubular section within the tubular housing volume, wherein the filtration section is movably sealed by the tubular housing and separates the tubular housing volume into a variable first tubular housing volume and a variable second tubular housing volume, wherein the filtration section comprises a first communication path between the raw side and the first tubular housing volume and a second communication path between the raw side and the second tubular housing volume so that, upon movement of the filtration section, blood in the first tubular housing volume flows through the first communication path to the raw side, wherein a blood plasma/serum may pass through the filter medium and the residual blood flows through the second communication path into the variable second tubular housing volume.

Thus, a blood filtering device is provided which is easy to handle and compact in volume. In particular, it is possible to simplify the complete process of taking blood from a patient and to carry out the filtering process since the above described blood filtering device enables the combination of blood treatment processes. In particular, the device enables conducting the filtering process by moving the filtration section with respect to the housing so that, when the first tubular housing volume increases, the second tubular housing volume decreases at the same time, and vice versa. The described blood filtering module enables taking blood from a patient and conducting the filtering process by means of the same module so that contamination and mistakes with respect to the identification of the blood, especially associated with decanting steps, may be avoided. In particular, it is not necessary to decant the blood after taking and before filtering since the filtering module or blood filtering device itself serves for taking blood. In addition, the blood filtering device only requires a minimum number of components and directly provides the serum or plasma obtained by the filtration process.

According to an exemplary embodiment, the filtration section comprises a first separator and a second separator, wherein the first separator is movably sealed by the tubular housing and separates the first tubular housing volume from the clean side, and the second separator is movably sealed by the tubular housing and separates the second tubular housing volume from the clean side.

Thus, a filtration section may be provided which can be moved within the tubular housing and a clean side may be provided between the first and second separators. In particular, a filter material may be provided between the first and the second separators so as to provide a raw side of the filter and a clean side of the filter and to further provide a separating filter medium between the first separator and the second separator so that the entire filter arrangement, including the first and second separators, may be moved as a unit within the tubular housing.

According to an exemplary embodiment, the first separator comprises the first communication path and the second separator comprises the second communication path, wherein the first separator and the second separator are fixedly mounted with respect to each other, and the filter medium extends between the first separator and the second separator.

Thus, the filtration section with the first and second separators and the filter medium in-between may be provided as a geometrically defined arrangement. The first separator and the second separator may be fixed with respect to each other. The fixation may be realized, for example, by a central post, which also may be a structure which may be used for moving the filtration section, for example, a piston rod. Alternatively, the first separator and the second separator may be fixedly mounted with respect to each other by a plurality of rods or structures, in particular, when it is desired to keep the central portion of the filtration section free of stabilizing structures. It should be noted that the filter medium may be a hollow fiber filter medium or a flat filter medium. It should be noted that, between the first separator and the second separator, mounting structures for the filter medium may also be provided as well as sealing structures for the filter medium and the respective volumes in order to separate the raw side of the filtration section from the clean side. It should be noted that, as an alternative, the separators may also be movable with respect to each other, which enables an adaption of the first and second variable volumes and the clean side volume. When the plasma/serum displaces the air at the clean side, the separators may be moved away from each other for compensating the displacement. At the same time, the sum of the blood-filled first and second variable volumes may decrease as the plasma/serum is removed; this leads to a reduction of the blood volume on the raw side and the first and second variable volumes. In this case, the filter medium may be a flexible hollow fiber, preferably helically wound to compensate the length variation.

According to an exemplary embodiment, the first tubular housing volume has a feeding opening for feeding blood to be filtered to the first variable tubular housing volume.

Thus, the blood filtering device may be used for taking blood from a patient, for example, when coupling a needle to the feeding opening, so as to directly deliver the blood from the patient into the first tubular housing volume. This may avoid a decanting process, as the blood is directly delivered from the patient into the blood filtering device.

According to an exemplary embodiment, the feeding opening comprises a Luer lock connector.

Thus, a standardized coupling may be provided, in particular for coupling supply lines to the feeding opening. It should be noted that instead of a Luer lock connector, also a Luer connector may be used as well as a standard cone for coupling a cannula or needle.

According to an exemplary embodiment, the feeding opening comprises a one-way valve allowing a flow only in a feeding direction.

Thus, it is possible to avoid a flow-out of the taken blood, in particular when operating the blood filtering device and generating a positive pressure in the first tubular housing volume in order to force the blood to be filtered to the filtration section. Although the opening may also be covered by a plug or cap, a valve provides an automatic closing without further manual action.

According to an exemplary embodiment, the blood filtering device further comprises a third separator, wherein the third separator separates the second tubular housing volume from an environment, wherein the third separator is movable along the tubular section of the tubular housing and is adapted to assume a terminal fixed sealing position with respect to the tubular housing.

Thus, the blood filtering device may be used for taking the blood directly from the patient, wherein the entire volume within the tubular housing may be increased when taking the blood, but for the filtration process may be kept in a defined position. In other words, when taking the blood from the patient, the blood filtering device will be used, and the filtration section moves together with the third separator in a distal direction in order to increase the entire volume. The entire volume may be defined by the first variable tubular housing volume, the second variable tubular housing volume, and the filtration section. The second tubular housing volume during the blood-taking process is kept small, as the third separator may directly abut the second separator when taking the blood, wherein the third separator may be fixed in a distal position when the blood taking process is terminated so that the filtration section can be moved in the opposite direction and the second tubular housing volume is increased. When moving the filtration section in the proximal direction, the blood in the first tubular housing section will be forced into the filtering section and the remaining blood components will leave the filtering section to enter the second tubular housing section. When moving the filtration section to the distal direction again, the blood in the second tubular housing volume will be forced to the filtration section and will leave the filtration section to enter the first tubular housing volume so that the process of filtering, i.e., the movement of the filtration section within the tubular housing, may be repeated.

According to an exemplary embodiment, the blood filtering device further comprises a rod extending through and along the tubular housing volume, wherein the rod with a first end is fixed to the filtration section, wherein the third separator has an opening through which a second end of the rod extends, wherein the rod is sealed relative to and movable through the opening of the third separator so that the filtration section may be moved within the tubular housing volume by the rod.

Thus, it is possible to operate the filtration section within the tubular housing by the rod extending through the opening of the third separator so that the second end of the rod may be reached by a user to operate the rod and thus the filtration section. It should be noted that the rod may further extend through the entire filtration section so as to couple both the first separator and the second separator to the rod and provide a stable filtration section geometry in combination with the rod.

According to an exemplary embodiment, the first end is fixed to the second separator of the filtration section so that the filtration section may be moved within the tubular housing volume by the rod.

According to an exemplary embodiment, the blood filtering device further comprises a resilient element functionally coupled between the rod and the tubular housing so as to provide a force for moving the filtration section in a direction toward the second tubular housing volume.

Thus, for moving the filtration section through and along the tubular housing in both directions, the user, for example, has to push the rod to move the filtration section into the first direction, i.e., the proximal direction, whereas the movement in the second direction, i.e., the distal direction, will be performed by the resilient element so that the user must only carry out a pushing action and the opposite movement is carried out by the resilient element. It should be noted that a resilient element may be provided also for supporting a movement in the opposite direction so that the user only carries out a pulling action and the opposite movement is performed by the resilient element.

According to an exemplary embodiment, the rod on the second end comprises a push button, wherein the resilient element is a coil spring between the push button and third separator.

Thus, the user may use the push button to operate the rod and thus the filtration section in order to move the filtration section in the proximal direction, wherein the coil spring will force the rod and thus the filtration section in the distal direction without further action by the user.

According to an exemplary embodiment, the clean side is defined by a volume bounded by the filter medium, a respective inner side of the first separator and of the second separator, and an inner wall of the tubular housing volume between the first separator and the second separator.

Thus, it is possible to provide an open filtration section, which may be monitored through a transparent housing. In particular, the result of the filtration process may be supervised.

According to an exemplary embodiment, the blood filtering device further comprises a plasma/serum outlet in the side wall of the tubular housing, wherein the plasma/serum outlet connects to the clean side of the filtration section.

Thus, it is possible to gain the plasma/serum through a defined outlet. In particular, when providing a so-called open filtration section, which means that the filtration section is also defined by an inner wall of the tubular housing volume, it is possible to provide the plasma/serum outlet in order to provide a connection to the filtration section, in particular to the clean side of the filtration section.

According to an exemplary embodiment, the movement of the filtration section is adapted such that the filtration section permanently overlaps the plasma/serum outlet.

Thus, it is possible to keep unfiltered blood away from the plasma/serum outlet so that no contamination of the gained plasma/serum by unfiltered blood can be expected.

According to an exemplary embodiment, the plasma/serum outlet is covered by a pierceable septum.

Thus, the clean side of the filtration section, i.e., the section where the plasma/serum is collected, may be hermetically sealed relative to the environment. However, it should be noted that the pierceable septum may be a membrane which is capable of allowing an overpressure at the clean side to escape so that an overpressure at the clean side of the filtration section may be avoided. It should be noted that, instead of a septum, a collecting volume may be provided, which may be coupled to the plasma/serum outlet in order to collect the plasma/serum. It should be noted that the external volume may be designed so as to collect the plasma/serum during the filtration process. The coupled volume may be decoupled from the blood filtering device to separate the blood filtering device from the external plasma/serum volume. The separate volume for collecting the plasma/serum may be a plunger or syringe arrangement or alternatively may be a blister. It should be noted that the external volume may be designed to be separated from the filtering device in such a way that the conduit between the filtration section, in particular, the clean side of the filtration section, and the separate volume for plasma/serum collection will be automatically closed when separating the external volume from the blood filtering device.

The simple and compact construction of the blood filtering device enables a manual shaking of the filter housing for effecting mixing of the blood sample to keep the suspension well-mixed and to avoid settling of the solid components. Further, when pre-treatment components are present, a stabilizing process may be obtained, for example, when mixing the whole blood with heparin. The closed and sealed filtering device can be disposed completely in the end when the critical materials are treated. No opening of the device is required. When employing a transparent material, a direct observation of the filtration process is possible.

It should be noted that the above features may also be combined. The combination of the above features may also lead to synergetic effects, even if not explicitly described in detail. These and other aspects of the invention will be become apparent from and be elucidated with reference to the embodiments described hereinafter.

BRIEF DESCRIPTION OF THE DRAWINGS

Exemplary embodiments of the present invention will be described in the following with reference to the following drawings.

FIG. 1 illustrates a blood filtering device according to an exemplary embodiment in a first state before filling in blood to be filtered.

FIG. 2 illustrates the blood filtering device of FIG. 1 in a second condition with blood to be filtered filled in.

FIG. 3 illustrates a cross-sectional view of the blood filtering device according to an exemplary embodiment of the invention.

DESCRIPTION OF THE INVENTION

Figure 4:
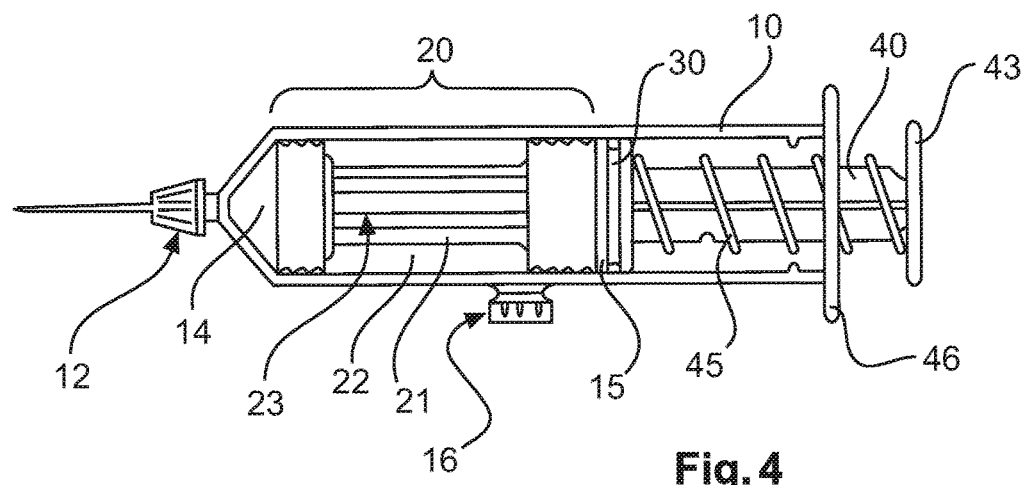
FIG. 4 illustrates an exemplary embodiment of the blood filtering device before filling in the blood to be filtered.

FIG. 1 illustrates a blood filtering device according to an exemplary embodiment of the invention. The blood filtering device 1 comprises a tubular housing 10 defining a tubular housing volume 11. Within the tubular housing volume 11, there is provided a variable first tubular housing volume 14 and a variable second tubular housing volume 15. Between the first tubular housing volume 14 and the second tubular housing volume 15, there is provided a filtration section 20. The filtration section 20 comprises a first separator 26 for separating the filtration section 20 from the variable first tubular housing volume 14, and a second separator 27 for separating the variable second tubular housing volume 15 from the filtration section 20. Between the first separator 26 and the second separator 27, there is provided a filter medium 23, wherein the filter medium separates a clean side 22 from a raw side 21.

Although not illustrated in FIG. 1, the separator 26 comprises a communication path to connect the variable first tubular housing volume 14 with the raw side 21 of the filtration section 20. The separator 27 comprises a communication path to connect the variable second tubular housing volume 15 with the raw side 21 of the filtration section 20. The blood filtering device 1 is provided with a feeding opening 12, wherein, for example, a needle can be coupled to the feeding opening 12 to take blood from a patient. The filtration section 20 is coupled to a rod 40 so as to operate and move forward and backward the filtration section 20 within the tubular housing volume 11. There is also provided a third separator 30, which third separator will be described in the following.

The blood filtering device 1 further comprises a plasma/serum outlet 16 to extract the gained plasma. The plasma/serum outlet 16 is in communication with the clean side 22 of the filtration section 20. It should be noted that the filter housing and the device may be produced of material which may be sterilized. It should be noted that several portions of the filtration device may be coated with heparin so that the blood condition may be kept sufficient for a filtration process. It should further be noted that the blood filtering device may have couplings or other elements to eliminate an overpressure or too strong a force applied to the respective variable filter volume. It should be noted that instead of a manual operation, also an electric or mechanical operation may be conducted, for example, when including the filtering device into an automated drive. It should also be noted that the filtration section or one of the variable blood reservoir volumes or the communication paths may be used as a reservoir for additives to improve the filtration process.

FIG. 2 illustrates the blood filtering device of FIG. 1 during the filling process, i.e., the needle has pierced the skin 2 of a patient to take blood. This can be achieved by pulling the rod 40 in the distal direction so that the filtration section 20 will be moved in the distal direction. The negative pressure in the variable first tubular housing volume 14 will suck the blood through the needle and the feeding opening 12 into the variable first tubular housing volume 14. It should be noted a check valve 13 may be provided in the feeding opening 12 to avoid escape of the taken blood 3, in particular when applying a positive pressure to the variable first tubular housing volume 14. When the intended amount of blood 3 has been taken into the variable first tubular housing volume 14, the filtration section 20 arrives with maximum travel in distal direction and impacts against the third separator 30. The third separator 30 will now snap into a fixation so as to define the variable second tubular housing volume 15 between the second separator 27 and the third separator 30.

Now, the blood filtering device 1 may be removed from the skin 2 and the filtration section 20 may be moved into the opposite, i.e., proximal direction, by pushing the rod 40. Now, the blood 3 will be forced through the communication paths in the first separator 26 to the raw side of the filtration section 20 so that the plasma/serum may pass through the filter medium and the remaining blood may exit the raw side through the communication paths in the second separator 27 to enter the variable second tubular housing volume 15. This will be described in further detail in the following.

FIG. 3 illustrates a cross-sectional view of the blood filtering device. The blood filtering device 1 comprises the tubular housing 10 defining the tubular housing volume 11. Within the tubular housing volume 11, there is provided the variable first tubular housing volume 14, the variable second tubular housing volume 15, and the filtration section 20. The filtration section 20 may be moved alternately from the proximal end to the distal end, and vice versa. The movement of the filtration section 20 may be carried out by means of the rod 40, which rod 40 may be connected to the filtration section 20 with its first end 41. At the second end 42 of the rod 40, there may be provided a push button 43 for operating the blood filtering device by a user. When pulling the filtration section 20 for the first time, the third separator 30, abutting the second separator 27, will be moved in the distal direction and will snap into a fixed position in order to remain in this position, even when the filtration section 20 is moved back in the proximal direction. The filtration section 20 comprises the first separator 26 and the second separator 27. Between the first and the second separators, there is provided a filter medium 23, which may be provided in form of a hollow fiber. It should be noted that any other filter material may be used also, e.g. a flat sheet medium. The filter medium 23 separates the volume between the first separator 26 and the second separator 27 into a raw side 21 and a clean side 22.

The raw side 21, here within the hollow fiber, is in communication with the variable first tubular housing volume 14 and the variable second tubular housing volume 15. For this purpose, a first communication path 24 is provided in the first separator 26 and a second communication path 25 is provided in the second separator 27. These communication paths 24 and 25 connect the variable first tubular housing volume 14 with the raw side 21 of the filtration section 20 and connect the variable second tubular housing volume 15 with the raw side 21. When moving the filtration section 20 within the tubular housing volume 11, the variable second tubular housing volume 15 decreases more and more and the pressure increases so that blood within the second tubular housing volume 15 is forced into the communication path 25 so as to arrive at the raw side 21. Owing to the pressure, the blood within the raw side 21 will be separated into the serum/plasma passing through the filter medium and arriving at the clean side 22 while the remaining blood exits the filtration section 20 through the first communication path 24 in the first separator 26 to arrive at the first tubular housing volume 14.

When the filtration section 20 arrives at the maximum distal position, the process will be reversed so that the blood in the variable first tubular housing volume 14 again enters the raw side 21. The blood will be filtered and the remaining blood will exit the filtration section through the second communication path 25 in the second separator 27 so as to arrive at the second tubular housing volume 15 again, until the filtration section 20 has arrived at the maximum proximal position.

In order to extract the gained plasma/serum from the clean side 22 of the filtration section 20, the serum/plasma may exit the blood filtering device through the plasma/serum outlet 16 provided in the wall of the housing. The plasma/serum outlet 16 may be covered by a pierceable septum 18.

It should be noted that the filtration section may be kept open, meaning that no additional wall may be provided between the first and second separators 26, 27, so that a direct communication between the clean side 22 and the plasma/serum outlet 16 is possible. This means, that the clean side 22 is defined by the inner walls of the separators 26, 27, the filter material or filter medium 23, and the inner wall 17 of the housing 10.

Figure 5:
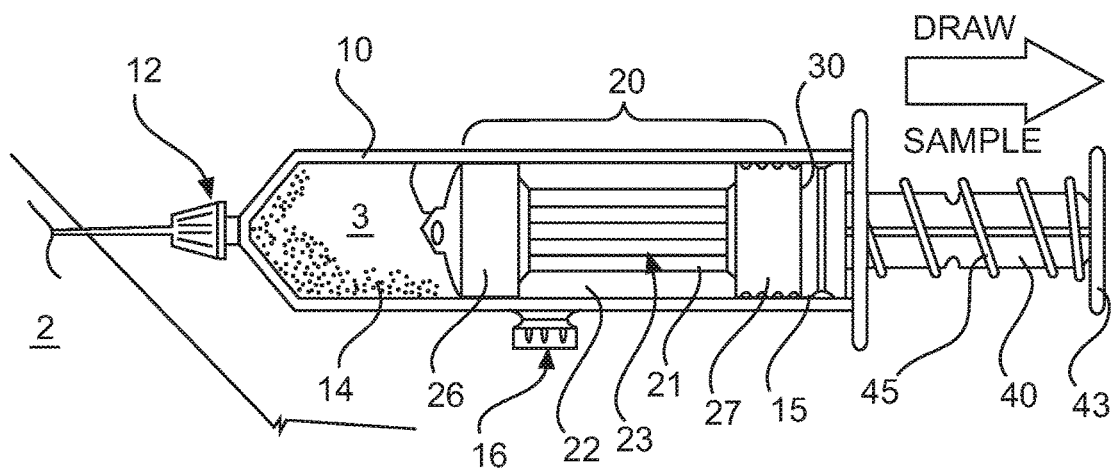
FIG. 5 illustrates the blood filtering device according to FIG. 4 during a filling process.

FIG. 4 illustrates the blood filtering device in a first situation with no blood present within the filtering device. In this situation, the filtration section 20 is in the proximal position and the third separator 30 abuts the second separator 27. FIG. 4 additionally illustrates a resilient element, here in the form of a spring 45, so that during operation the user must only perform a pushing movement, wherein the opposite movement will be performed by the resilient member. The blood filtering device punctures the skin 2 of the patient with a needle, as described in FIG. 5. The needle may not be part of the blood filtering device as such and may be separable. Now, the user may pull the rod 40 by the push button 43 so as to pull the filtration section 20 from the proximal position into the distal position so that blood enters the first tubular housing volume 14.

Figure 6:
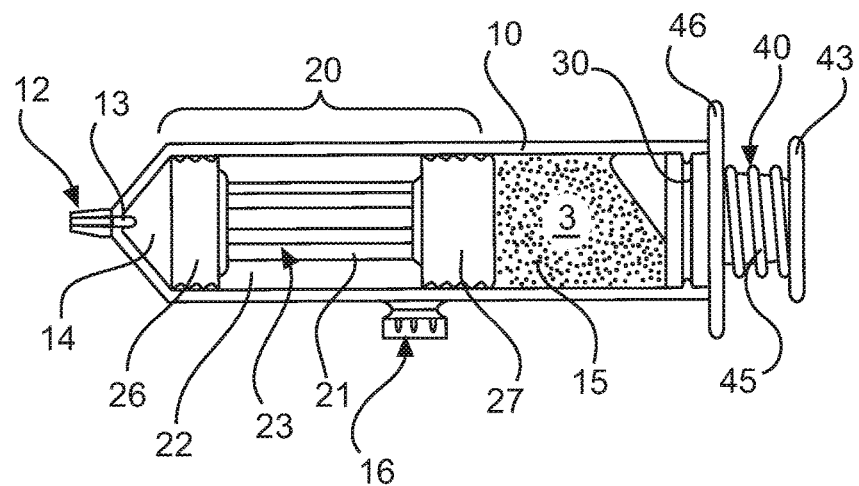
FIG. 6 illustrates the blood filtering device of FIG. 4 after having conducted the first filtering iteration.

When the maximum amount of blood 3 has entered the first tubular housing volume 14, the filtration section 20 is in the maximum distal position, and the third separator 30 clicks into a fixed position. Now, the blood filtering device may be removed from the patient, as will be described with respect to FIG. 6. When having removed the device from the patient, which however is not mandatory but facilitates handling, the user may push the rod 40 by means of the push button 43 so that the filtration section 20 will be pushed in the proximal direction. The blood 3 from the first volume 14 will be forced into the filtration section 20 and the remaining blood will exit into the second tubular housing volume 15. It should be noted that the third separator 30 remains in the fixed position so that the second tubular housing volume 15 now is increased by pushing the filtration section 20 back in the proximal direction; at the same time, the first tubular housing volume 14 decreases.

When the user now releases the push button 43, the resilient member in the form of spring 45 will push back the push button 43 so that the filtration section 20 will again move in the distal direction and force the blood through the filtration section 20 from the second tubular housing volume 15 into the first tubular housing volume 14. This process of cross-flow filtration can be repeated as needed, until a sufficient amount of plasma/serum is collected at the clean side 22 of the filtration section 20 and can be extracted from the plasma/serum outlet opening 16. A check valve 13 may prevent unintended escape of blood 3 out of the variable first tubular housing volume 14. It should be noted that also a different closing mechanism may be used, for example, a permanent closing when removing, for example, the needle from the blood filtering device.

Figure 7:
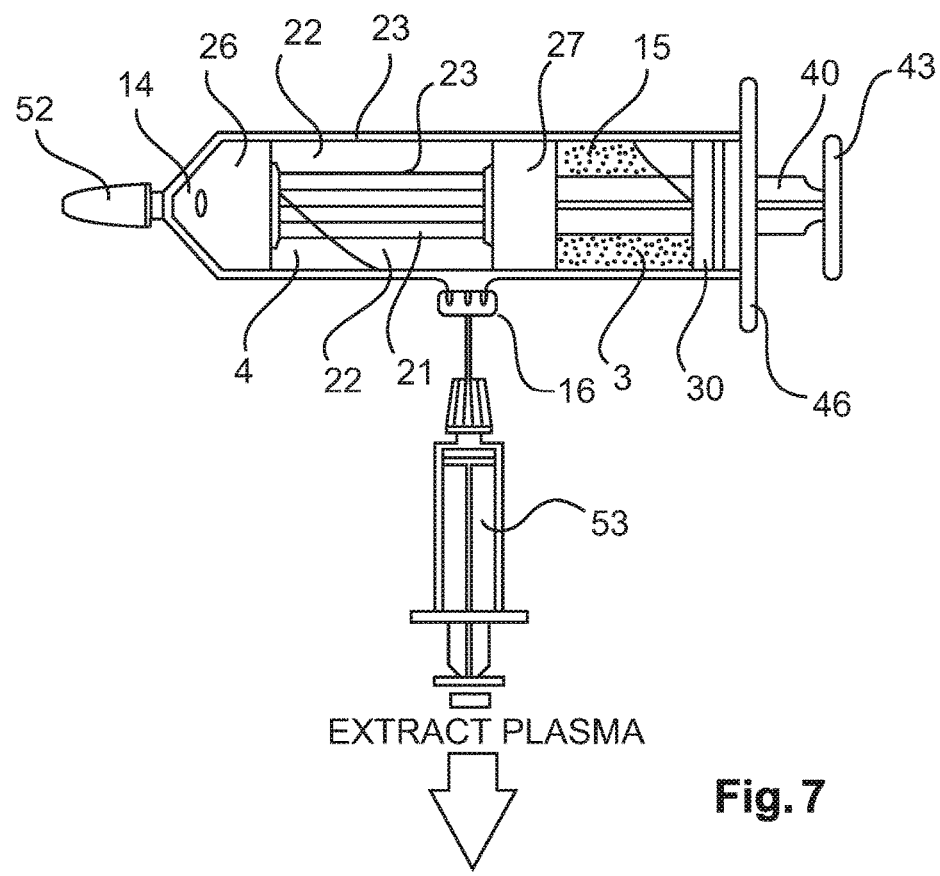
FIG. 7 illustrates an exemplary embodiment of the blood filtering device after the filtering process when extracting the gained plasma/serum.

FIG. 7 now illustrates the process of extracting the plasma. When having terminated the entire filtering process by repeated movement of the filtration section 20 within the tubular housing volume 11, the gained plasma at the clean side 22 of the filtration section 20 may be extracted by way of a plasma/serum reservoir or a syringe or a container 53. It should be noted that the plasma/serum reservoir or syringe or generally a container may be incorporated into the blood filtering device so that the pierceable septum may be avoided. However, in this case it appears to be reasonable to provide a connection which reliably closes the openings when removing the plasma/serum reservoir 53 from the blood filtering device.

Figure 8:
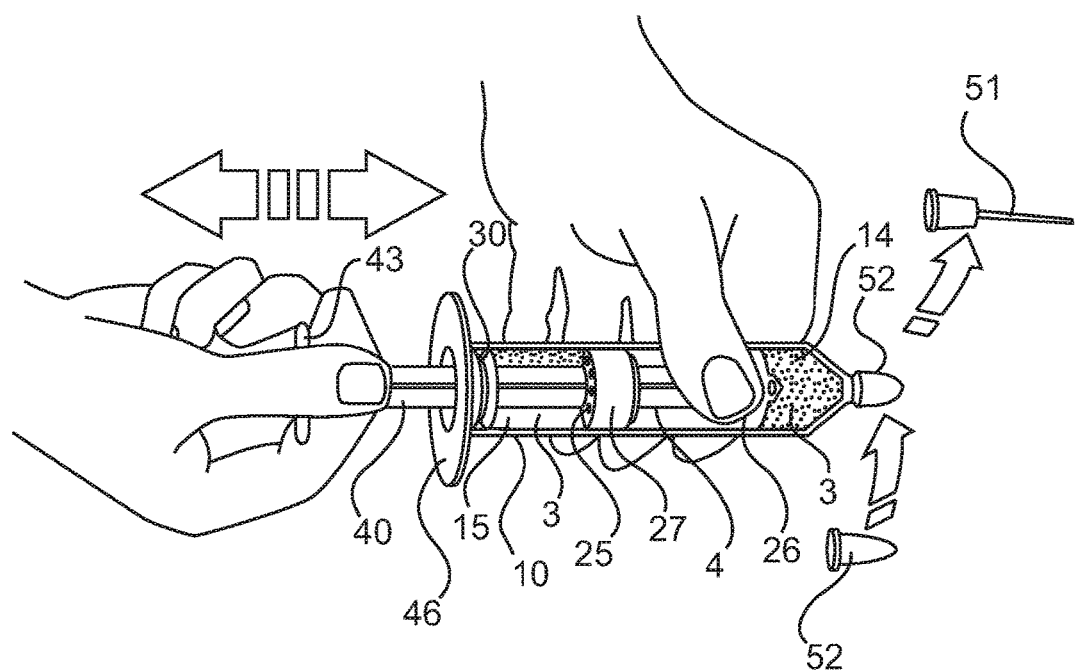
FIG. 8 illustrates an exemplary embodiment of the blood filtering device and its operation during use.

For the filtering process, the needle 51 may be removed and the opening may be closed by a cap 52, as can be seen in FIG. 8.

FIG. 8 also illustrates handling by a user in that a user can push and pull the rod 40 to operate the filtering process. It should be noted that also a collar 46 may be provided which may facilitate the process of pushing when the user pushes the push button 43.

While specific embodiments of the invention have been shown and described in detail to illustrate the inventive principles, it will be understood that the invention may be embodied otherwise without departing from such principles.

What is claimed is:

1. A blood filtering device comprising:
    a tubular housing including a tubular section and defines a tubular housing volume therein, the tubular housing elongated along an axis defining an axial direction;
    a filtration section entirely arranged within and enclosed by the tubular housing, the filtration section including:
        a blood filter medium having a raw side and an opposite clean side,
        wherein the a blood filter medium is permeable for blood plasma/serum for filtering blood plasma/serum from blood through the blood filter medium to present separated blood plasma/serum at the clean side;
        a first separator arranged on an axial end of the blood filter medium,
        wherein the first separator movably seals against in inner side of the tubular section to subdivide the tubular housing volume of the tubular housing;
        a second separator arranged on an opposite axial end of the blood filter medium,
        wherein the second separator movably seals against in inner side of the tubular section to further subdivide the tubular housing volume of the tubular housing;
    wherein the filtration section having the blood filter blood filter medium, first separator and second separator together form the filtration section;
    wherein the filtration section is axially movable along the tubular section within the tubular housing volume while the first and second separators continue to seal against the tubular section of the tubular housing;
    wherein the filtration section is movably sealed relative to the tubular housing and separates the tubular housing volume into a variable first tubular housing volume and a variable second tubular housing volume;
    wherein the filtration section comprises a first communication path between the raw side and the first tubular housing volume and further comprises a second communication path between the raw side and the second tubular housing volume so that, when moving the filtration section in the tubular housing, blood in the first tubular housing volume flows through the first communication path to the raw side and the blood plasma/serum passes through the blood filter medium to the clean side while the residual blood flows through the second communication path into the variable second tubular housing volume.

2. The blood filtering device according to claim 1, wherein
    the first separator is movably sealed relative to the tubular housing and separates the first tubular housing volume from the clean side, and
    wherein the second separator is movably sealed relative to the tubular housing and separates the second tubular housing volume from the clean side.

3. The blood filtering device according to claim 2, wherein
    the first communication path is provided in the first separator and
    the second communication path is provided in the second separator,
    wherein the first separator and the second separator are fixedly mounted relative to each other, and
    wherein the filter medium extends between the first separator and the second separator.

4. The blood filtering device according to claim 2, further comprising a third separator, wherein the third separator separates the second tubular housing volume from an outside environment, wherein the third separator is movable along the tubular section of the tubular housing and is adapted to assume a terminal fixed sealing position relative to the tubular housing.

5. The blood filtering device according to claim 4, further comprising
    a rod extending through and along the tubular housing volume,
    wherein the rod comprises
        a first end fixed to the filtration section and
        further comprises a second end extending through an opening of the third separator to an exterior of the tubular housing,
        wherein the rod is sealed relative to and movable in the opening of the third separator so that the filtration section is movable within the tubular housing volume by actuating the rod.

6. The blood filtering device according to claim 5, wherein
   the first end of the rod is fixed to the second separator of the filtration section.

7. The blood filtering device according to claim 5, further comprising
   a resilient element functionally coupled between the rod and the tubular housing so as to provide a force that moves the filtration section in a direction toward the second tubular housing volume.

8. The blood filtering device according to claim 7, wherein
   the second end of the rod comprises a push button and
   wherein the resilient element is a coil spring arranged between the push button and the third separator.

9. The blood filtering device according to claim 2, wherein
   the clean side is defined by a volume bounded by the filter medium, an inner side of the first separator facing the second separator, an inner side of the second separator facing the first separator, and an inner wall of the tubular housing extending between the first separator and the second separator and facing the filter medium.

10. The blood filtering device according to claim 1, further comprising
    a plasma/serum outlet in a side wall of the tubular housing,
    wherein the plasma/serum outlet connects to the clean side.

11. The blood filtering device according to claim 10, wherein
    a range of movement of the filtration section is selected such that the filtration section permanently overlaps the plasma/serum outlet.

12. The blood filtering device according to claim 11, wherein
    the plasma/serum outlet is covered by a pierceable septum.

13. The blood filtering device according to claim 1, wherein
    the first tubular housing volume comprises a feeding opening through which blood to be filtered is fed into the first tubular housing volume.

14. The blood filtering device according to claim 13, wherein
    the feeding opening comprises a Luer lock connector.

15. The blood filtering device according to claim 13, wherein
    the feeding opening comprises a one-way valve permitting a flow only in a feeding direction into the first tubular housing volume.

\* \* \* \* \*